United States Patent [19]

Girard et al.

[11] Patent Number: 5,252,599
[45] Date of Patent: Oct. 12, 1993

[54] HETEROARYLNAPHTHALENE HYDROXY ACIDS AS INHIBITORS OF LEUKOTRIENE BIOSYNTHESIS

[75] Inventors: Yves Girard, Ile Bizard; Rejean Fortin, Montreal-Nord; Daniel Delorme; Daniel Dube, both of St. Lazare; Pierre Hamel, Vimont; Yves Ducharme, Montreal; John W. Gillard, Raie d'Urfe, all of Canada

[73] Assignee: Merck Frosst Canada, Inc., Quebec, Canada

[21] Appl. No.: 936,810

[22] Filed: Aug. 27, 1992

[51] Int. Cl.⁵ ............... A61K 31/35; C07D 309/10
[52] U.S. Cl. .................. 514/456; 549/330; 549/362; 549/366; 549/397; 549/398; 549/414
[58] Field of Search ............ 549/397, 414, 330, 362, 549/366, 398; 514/456

[56] References Cited

U.S. PATENT DOCUMENTS

| | | |
|---|---|---|
| 4,486,445 | 12/1984 | Patel et al. |
| 4,937,373 | 6/1990 | Carson et al. |
| 5,124,350 | 6/1992 | Djuric et al. ............... 514/456 |

FOREIGN PATENT DOCUMENTS

| | | |
|---|---|---|
| 0188248 | 7/1986 | European Pat. Off. |
| 0351194 | 1/1990 | European Pat. Off. |
| 0375368 | 6/1990 | European Pat. Off. |
| 0375404 | 6/1990 | European Pat. Off. |
| 0375452 | 6/1990 | European Pat. Off. |
| 0380982 | 8/1990 | European Pat. Off. |
| 0381375 | 8/1990 | European Pat. Off. |
| 0385662 | 9/1990 | European Pat. Off. |
| 0385663 | 9/1990 | European Pat. Off. |
| 0385679 | 9/1990 | European Pat. Off. |
| 0385680 | 9/1990 | European Pat. Off. |
| 0409413 | 1/1991 | European Pat. Off. |
| 0462812 | 12/1991 | European Pat. Off. |
| 0462830 | 12/1991 | European Pat. Off. |

OTHER PUBLICATIONS

The Merck Index, 11th ed., 5154, p. 829 (1989).

Primary Examiner—Marianne M. Cintins
Assistant Examiner—John Peabody
Attorney, Agent, or Firm—Joseph F. DiPrima; Mark R. Daniel; David A. Muthard

[57] ABSTRACT

Compounds having the formula I:

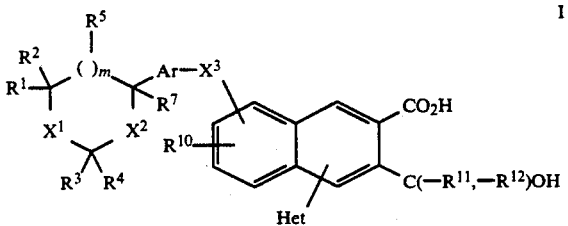

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

10 Claims, No Drawings

HETEROARYLNAPHTHALENE HYDROXY ACIDS AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated at $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

European patent application 375,404 (Jun. 27, 1990) describes certain naphthalene-containing heterocyclic ethers of structure A which are inhibitors of the enzyme 5-lipoxygenase. EP application 375,452 (Jun. 27, 1990) describes naphthalene-containing hydrocarbon ethers of structure B which are reported to possess the same activity. EP application 462,830 (Dec. 27, 1991) describes bicyclic heterocycle-containing hydrocarbon ethers of structure C which are reported to possess the same activity. All these series of prior art compounds differ significantly from the present invention in that they lack both the aryl substituent and the additional fused ring of the present compounds.

A series of natural products known as the justicidins are referred to in the Merck Index, 11th edition, 1989, no. 5154. The justicidins differ considerably from the present compounds in that they are lacking the large pyranylphenyl group.

Hence the compounds of the present invention are completely novel and unexpectedly have biological activity as leukotriene biosynthesis inhibitors.

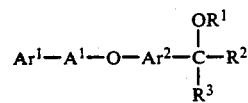

A EP 375,404
ICI-Pharma

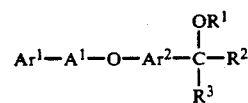

B EP 375,462
ICI-Pharma

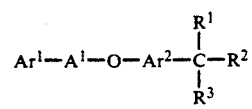

C EP 462,830
ICI-Pharma

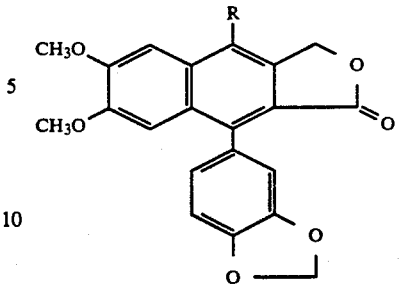

Justicidins, Merck Index No. 5154

SUMMARY OF THE INVENTION

The present invention relates to heteroarylnaphthalene hydroxy acids having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The compounds of the present invention may be represented by the formula I:

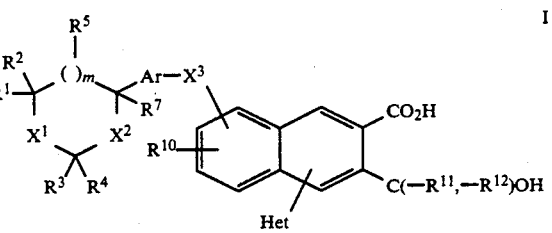

wherein:
$R^1$, $R^5$, and $R^{11}$ is each independently H, OH, lower alkyl, or lower alkoxy;
$R^2$ is H, lower alkyl, or together with $R^1$ forms a double bonded oxygen (=O);
$R^3$ is H, lower alkyl, hydroxy lower alkyl, lower alkoxy lower alkyl, or is joined to $R^1$ to form a carbon bridge of 2 or 3 carbon atoms or a monooxa carbon bridge of 1 or 2 carbon atoms, said bridge optionally containing a double bond;
$R^4$, $R^{12}$, and $R^{14}$ is each independently H or lower alkyl;
$R^6$ is H or lower alkyl, or two $R^6$ groups on the same or adjacent carbons can form a saturated ring of 3 to 8 members;
$R^7$ is H, OH, lower alkyl, lower alkoxy, lower alkylthio, or lower alkylcarbonyloxy;
$R^8$, is H, halogen, lower alkyl, lower alkoxy, $CF_3$, CN, $COR^{14}$, or a non-bonded electron pair;
$R^9$ and $R^{10}$ is each independently H, lower alkyl, lower alkoxy, hydroxy lower alkyl, lower alkoxy lower alkyl, lower alkylthio lower alkyl, lower alkylthio lower alkylcarbonyl, $(R^8)_2$-phenylthio lower alkyl, halogen, CN, $NO_2$, $CF_3$, $N_3$, $N(R^{13})_2$, $NR^{13}COR^{14}$, $NR^{13}CON(R^{13})_2$, $SR^{15}$, $S(O)R^{15}$, $S(O)_2R^{15}$, $S(O)_2N(R^{13})_2$, $COR^{14}$, $CON(R^{13})_2$, $CO_2R^{14}$, $C(R^{14})_2OC(R^{14})_2$—$CO_2R^{14}$, or $C(R^{14})_2CN$;

$R^{10}$ is attached to either ring of the naphthalene ring system;

$R^{13}$ is H or lower alkyl, or two $R^{13}$ groups attached to the same nitrogen may form a saturated ring of 5 or 6 members, optionally containing a second heteroatom chosen from O, S, or $NR^4$;

$R^{15}$ is lower alkyl, phenyl-$(R^8)_2$, or $CF_3$;

$X^1$ is O, S, S(O), $S(O)_2$, or $C(R^6)_2$ $X^2$ is O, S, or $C(R^6)_2$ or a bond;

$X^3$ is $C(R^6)_2S$, $SC(R^6)_2$, $C(R^6)_2O$, $OC(R^6)_2$, $CR^6=CR^6$, $C(R^6)_2C(R^6)_2$, O, or S;

Ar is arylene$(R^8)_2$ wherein arylene is a 5-membered aromatic ring containing one O or S and 0–2 nitrogen atoms; a 5-membered aromatic ring containing 1–3 nitrogen atoms; a 6-membered aromatic ring containing 0–3 nitrogen atoms; 2- or 4-pyranone; or 2- or 4-pyridinone;

Het is heteroaryl$(R^9)_2$ wherein heteroaryl is a 5-membered aromatic ring containing one O or S and 0–3 nitrogen atoms; a 5-membered aromatic ring containing 1–4 nitrogen atoms; a 6-membered aromatic ring containing 1–3 nitrogen atoms; 2- or 4-pyranone; 2- or 4-pyridinone; a bicyclic 8-, 9-, 10-membered aromatic ring containing 1–4 heteroatoms chosen independently from O, S, and N.

Het is attached to either ring of the naphthalene ring system; and m is 0 or 1;

or a pharmaceutically acceptable salt thereof.

It will be obvious to one skilled in the art that if $R^{11}$ is OH or lower alkoxy on the same carbon atom as the OH group of I, the elements of water or an alcohol may be lost to give an aldehyde or ketone.

A preferred embodiment of the present invention is represented by Formula Ia:

Ia wherein the substituents are as defined for Formula I, or a pharmaceutically acceptable salt thereof.

Another embodiment of the present invention is represented by Formula Ib

Ib wherein:

$R^1$ is H, Me, or OMe;

$R^3$ is H or Me;

$R^1$ and $R^3$ together are —CH=CH—, —$CH_2CH_2$—, —$OCH_2$—, or —$CH_2O$—;

$R^5$ is H or $OCH_3$;

$R^7$ is OH, $OCH_3$, or $CH_2CH_3$;

Ar is Phe; 5,3-Pye; 6,2-Pye; 2,4-Pye; or 4,2-Pye; and

Het is 3-Fu or 3-Th;

or a pharmaceutically acceptable salt thereof.

DEFINITIONS

The following abbreviations have the indicated meanings:

| | | |
|---|---|---|
| Ac | = | acetyl |
| Bn | = | benzyl |
| c-Bu | = | cyclobutyl |
| Bu$_4$NF | = | tetrabutylammonium fluoride |
| c-Pen | = | cyclopentyl |
| c-Pr | = | cyclopropyl |
| c-Hex | = | cyclohexyl |
| i-Pr | = | isopropyl |
| n-Pr | = | normal propyl |
| n-Bu | = | normal butyl |
| i-Bu | = | isobutyl |
| s-Bu | = | secondary butyl |
| t-Bu | = | tertiary butyl |
| Et | = | ethyl |
| Fu | = | 2- or 3-furyl |
| Me | = | methyl |
| Ph | = | phenyl |
| Py | = | 2-, 3-, or 4 pyridyl |
| Th | = | 2- or 3-thienyl |
| DHP | = | 3,4-dihydro-2H-pyran |
| DMF | = | N,N-dimethylformamide |
| DMSO | = | dimethylsulfoxide |
| NBS | = | N-bromosuccinimide |
| PCC | = | pyridinium chlorochromate |
| Phe | = | benzenediyl |
| Pye | = | pyridindiyl |
| Super-Hydride | = | lithium triethylborohydride |
| TFA | = | trifluoroacetic acid |
| THF | = | tetrahydrofuran |

Alkyl is intended to include linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, and cyclohexylacetyl. By way of illustration, the 2-methylbutanoyl group signifies —$COCH(CH_3)CH_2CH_3$.

"Hydroxy lower alkyl" means a lower alkyl group carrying a hydroxy group; e.g., —$CH_2CH(OH)CH_2CH_3$.

"Lower alkoxy lower alkyl" means a lower alkyl group carrying a lower alkoxy group; e.g., —$CH_2CH_2OCH_3$.

"Lower alkylthio" means alkylthio groups of from 1 to 7 carbon atoms of a straight, branched, or cyclic configuration. Examples of lower alkylthio groups include methylthio, ethylthio, isopropylthio, cyclobutylthio, and the like.

"Lower alkylthio lower alkyl" means a lower alkyl group carrying a lower alkylthio group; e.g., —CH$_2$CH$_2$S-c-Pr.

"Lower alkylthio lower alkylcarbonyl" means a lower alkylcarbonyl group carrying a lower alkylthio group; e.g., —COCH$_2$SCH$_2$CH$_3$.

"(R$^8$)$_2$-phenylthio lower alkyl" means a lower alkyl group carrying a phenylthio group which in turn carries two R$^8$ substituents; e.g., —CH$_2$CH$_2$S-Ph-4-CN.

Examples of "arylene" are benzene, furan, thiophene, isoxazole, isothiazole, oxazole, thiazole, 1,3,4-oxadiazole, 1,3,4-thiadiazole, 1,2,5-oxadiazole, 1,2,5-thiadiazole, pyrrole, pyrazole, imidazole, 1,3,4-triazole, pyridine, pyrazine, pyrimidine, pyridazine, 1,2,3-triazine, 1,2,4-triazine, 1,3,5-triazine, and the like.

Examples of "heteroaryl" are furan, thiophene, oxazole, thiazole, isoxazole, isothiazole, 1,3,4-oxadiazole, 1,3,4-thiadiazole, 1,2,5-oxadiazole, 1,2,5-thiadiazole, pyrrole, pyrazole, imidazole, 1,3,4-triazole, tetrazole, pyridine, pyrazine, pyrimidine, pyridazine, 1,2,3-triazine, 1,2,4-triazine, 1,3,5-triazine, thieno[2,3-b]furan, thieno[3,2-b]pyrrole, indole, benzofuran, benzothiophene, benzimidazole, benzoxazole, benzothiazole, benzo[2,1,3]thiadiazole, thieno[3,2-b]pyridine, furano[2,3-c]pyridine, furano[3,2-b]pyridine, quinoline, isoquinoline, quinoxaline, quinazoline, cinnoline, phthalazine, 1,8-naphthyridine, pteridine, and the like.

Halogen includes F, Cl, Br, and I.

It is intended that the definitions of any substituent (e.g., R$^6$, R$^8$, etc.) in a particular molecule be independent of its definitions elsewhere in the molecule. Thus, C(R$^6$)$_2$S represents CHCH$_3$S, CH$_2$S, C(CH$_3$)$_2$S, etc.

OPTICAL ISOMERS—DIASTEREOMERS—GEOMETRIC ISOMERS

Some of the compounds described herein contain one or more asymmetric centers and may thus give rise to diastereomers and optical isomers. The present invention is meant to comprehend such possible diastereomers as well as their racemic and resolved, enantiomerically pure forms, and pharmaceutically acceptable salts thereof.

Some of the compounds described herein contain olefinic double bonds, and unless specified otherwise, are meant to include both E and Z geometric isomers.

SALTS

The pharmaceutical compositions of the present invention comprise a compound of Formula I as an active ingredient or a pharmaceutically acceptable salt, thereof, and may also contain a pharmaceutically acceptable carrier and optioncally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

UTILITIES

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation, and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia, and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) multiple sclerosis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as CCl$_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are: (A) an ethanol-induced lesion assay, and (B) an indomethacin-induced ulcer assay and are described in EP 140,684.

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001-1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

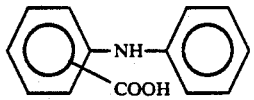

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

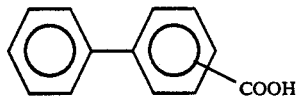

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

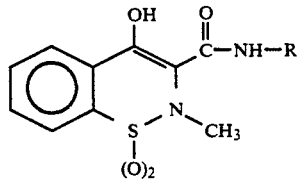

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., *Pharmaprojects*), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an H$_1$- or H$_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K$^+$/H$^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compounds of the present invention can be prepared according to the following methods. Temperatures are in degrees Celsius. The substituents are the same as in Formula I except where defined otherwise.

SCHEME I

The route which is used to prepare the lactone VI is outlined in Scheme I. The heteroaryl carboxaldehyde II is converted to the thioacetal III by treatment with thiophenol in the presence of a Lewis-Acid such as $BF_3.Et_2O$ in an organic solvent such as isopropyl acetate. The thioacetal III is then converted to the lactone V by treatment with a base such as n-BuLi in an organic solvent such as THF followed by the successive additions of 2-(5H) furanone and the benzyloxy benzaldehyde IV in an organic solvent such as THF followed by quenching with an acid such as HOAc. The cyclization, dehydration and debenzylation are achieved simultaneously by heating the lactone V in the presence of an acid such as TFA, and using thioanisole as organic solvent providing the lactone VI.

SCHEME II

The preparation of compounds of Formula I (wherein $X^3 = -C(R^6)_2O-$) is described in Scheme II. A first method requires coupling of the naphthol VI with a benzylic halide or activated alcohol of type VII (wherein $X = Cl, Br, I, OMs, OTs$) in a polar organic solvent such DMF in the presence of an inorganic base such as $Cs_2CO_3$.

In an alternate procedure, the naphthol VI is condensed with the benzylic alcohol VII (wherein $X = OH$) in the presence of a phosphine such as $Ph_3P$ and an azodicarboxylate diester, in a solvent such as THF, to afford the lactone VIII.

SCHEME III

The synthesis of compounds of Formula I (wherein $X^3 = -OCH_2-$) is described in Scheme III. The phenol lactone VI may be converted to the triflate IX by treatment with trifluoromethanesulfonic anhydride in the presence of an organic base such as pyridine in a solvent such as $CH_2Cl_2$. Subsequent treatment of IX in a solvent such as DMSO/MeOH with an organic base such as triethylamine, a phosphine such as 1,1'-bis(diphenylphosphino)ferrocene, a palladium(II) salt such as palladium(II)acetate under an atmosphere of carbon monoxide will lead to the ester X. The hydrolysis of the ester X may be achieved using an inorganic base such as lithium hydroxide in water and the resulting acid XI may be reduced to the alcohol XII by treatment with a chloroformate such as isopropyl chloroformate in the presence of an organic base such as triethylamine in an organic solvent such as THF, followed by addition of a reducing agent such as sodium borohydride in water. The alcohol XII may be then converted to the halide XIII by treatment with triphenylphosphine, imidazole and $CBr_4$ in an organic solvent such as $CH_2Cl_2$. Coupling of halide XIII with the appropriate phenol XIV in an organic solvent such as DMF using an inorganic base such as $K_2CO_3$ provides the lactone XV.

SCHEME IV

Scheme IV illustrates the conversion of lactone VIII (Scheme II) and lactone XV (Scheme III) to lactone XVII. Lactones VIII and XV may be alkylated by treatment with a strong base such as lithium diisopropylamide in a strong solvent such as THF, followed by quenching with an alkyl halide such as methyl iodide. A second alkylation may be achieved by using the same conditions. Conversion of lactones VIII and XV to lactone XVII (wherein $R^{11} = OH$, $R^{12} = H$) may be achieved by a hydrolytic process using an inorganic base such as NaOH in a solvent such as $EtOH/H_2O$ to provide the carboxylate salt XVI, followed by an oxidation step using an oxidizing agent such as pyridinium chlorochromate in an organic solvent such as $CH_2Cl_2$. The reaction of lactone XVII ($R^{11} = OH$, $R^{12} = H$) with a lower alkyl Grignard or lithium reagent may yield compound I ($R^{11}$ = lower alkyl, $R^{12} = H$).

The hydrolysis of lactones VIII (Scheme II), XV (Scheme III), and XVII (Scheme IV) using an inorganic base such as NaOH in a solvent such as $EtOH/H_2O$ provides compounds of Formula I of the present invention. Compound XVI in Scheme IV is also representative of the compounds of Formula I. It will be evident to one skilled in the art that a variety of cationic salt forms of I can be prepared in this way or by cation exchange processes.

SCHEME I
PREPARATION OF LACTONE INTERMEDIATES

SCHEME I
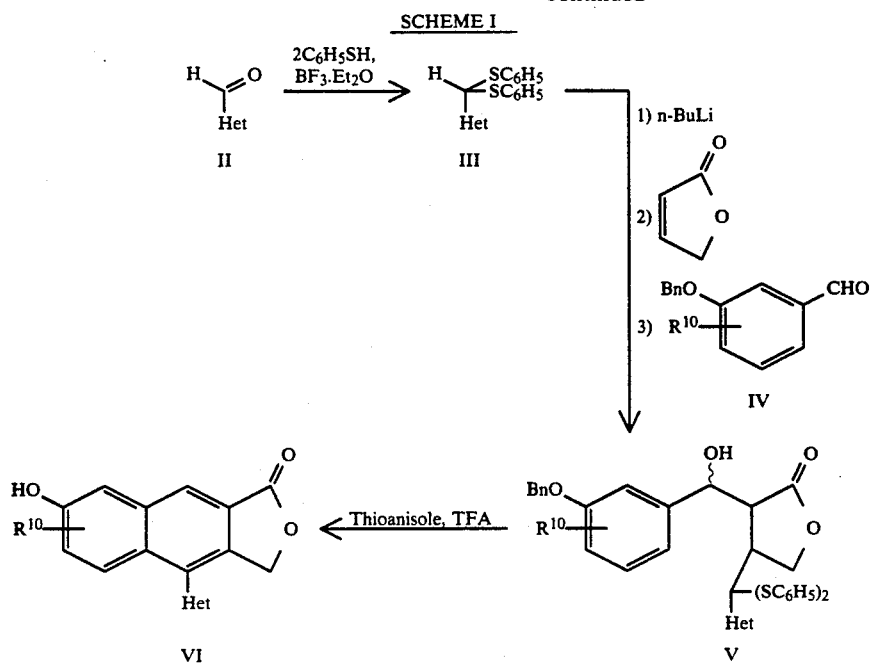
SCHEME II
PREPARATION OF FINAL PRODUCTS
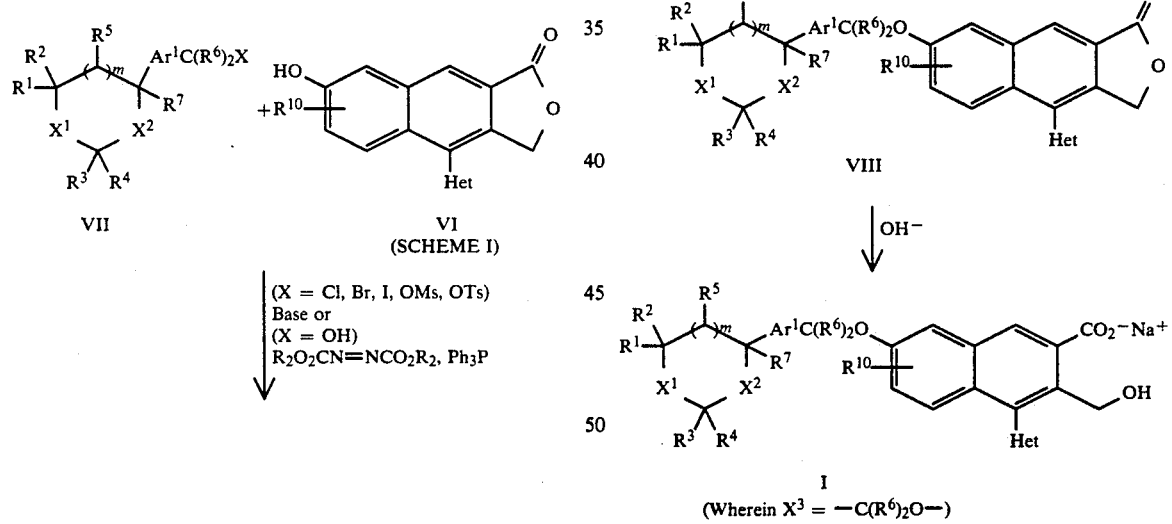
SCHEME III
PREPARATION OF FINAL PRODUCTS
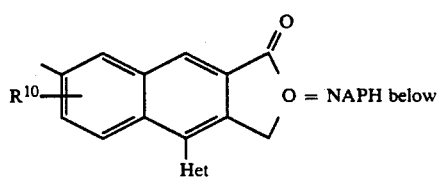

-continued
SCHEME III
HO—NAPH ⟶ TfO-NAPH ⟶ MeO₂C—NAPH
VI         IX           X
(SCHEME I)
                          ↓
BrCH₂—NAPH ⟵ HOCH₂—NAPH ⟵ HO₂C—NAPH
XIII            XII              XI
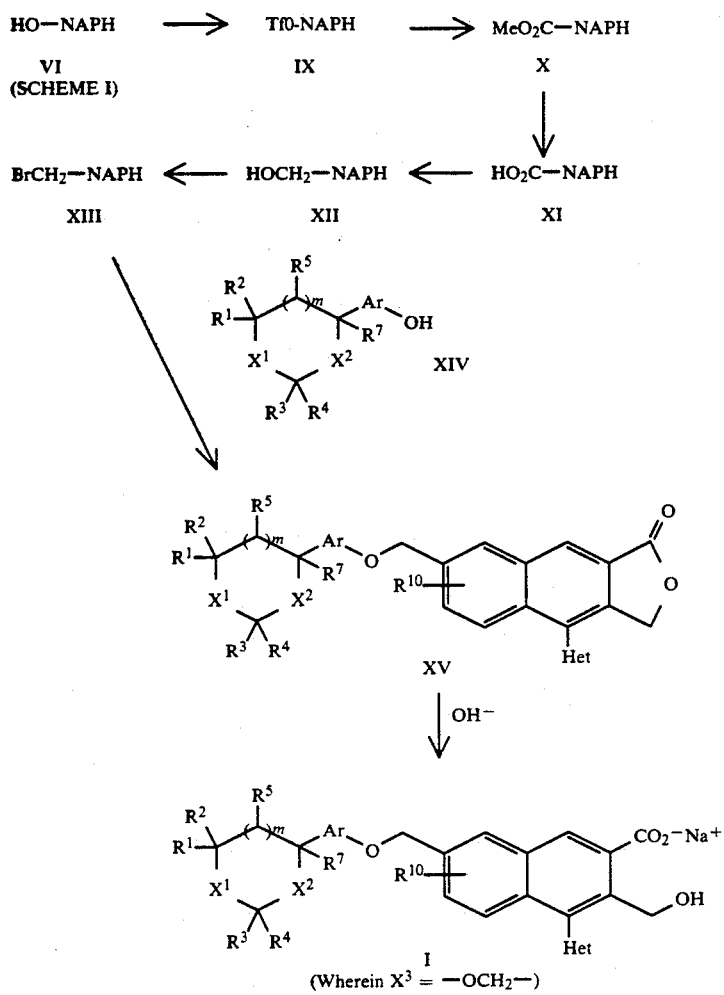
(Wherein $X^3$ = —OCH₂—) I
SCHEME IV
PREPARATION OF FINAL PRODUCTS
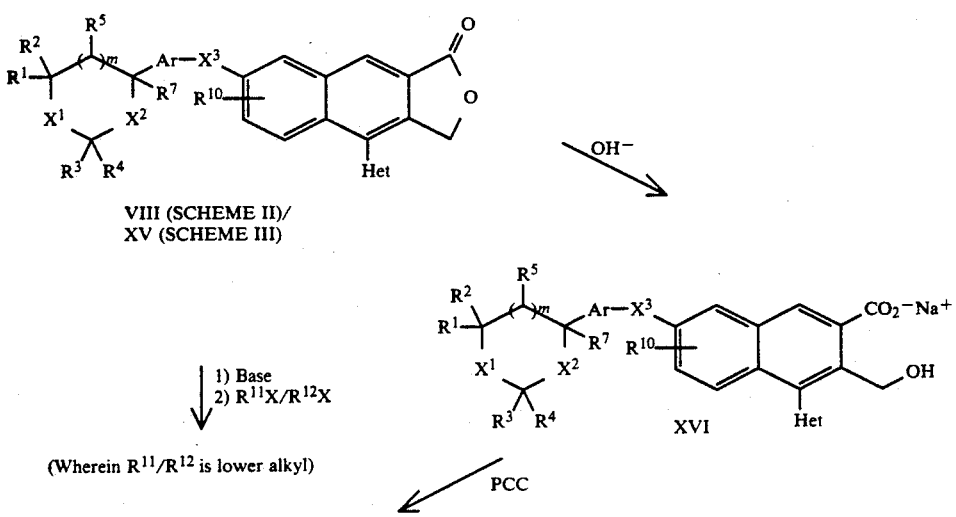
VIII (SCHEME II)/
XV (SCHEME III)
1) Base
2) $R^{11}X/R^{12}X$
(Wherein $R^{11}/R^{12}$ is lower alkyl)
PCC -continued
SCHEME IV
PREPARATION OF FINAL PRODUCTS (Wherein $R^{11}$ is hydroxyl)
(and $R^{12}$ is H)

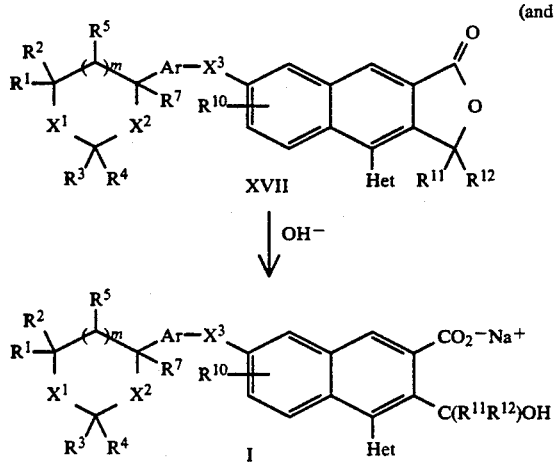

REPRESENTATIVE COMPOUNDS

Table I illustrates compounds representative of the present invention.

TABLE I

| EX. | $R^1$ | $R^3$ | $R^5$ | $R^7$ | Ar | Het |
|---|---|---|---|---|---|---|
| 1 | H | H | H | OH | Phe | 3-Fu |
| 2 | H | H | H | OMe | Phe | 3-Fu |
| 3 | H | H | H | OH | Phe | 3-Py |
| 4 | H | H | H | OH | Phe | 2-Fu |
| 5 | —CH=CH— | | H | OH | Phe | 3-Fu |
| 6 | —CH$_2$CH$_2$— | | H | OH | Phe | 3-Fu |
| 7 | H | H | H | OH | 5,3-Pye | 3-Fu |
| 8 | —CH$_2$O— | | H | OH | Phe | 3-Fu |
| 9 | H | H | H | OH | Phe | 3-Th |
| 10 | H | H | H | OH | 5,3-Pye | 3-Th |
| 11 | —CH$_2$O— | | H | OH | Phe | 3-Th |
| 12 | —CH$_2$O— | | H | OMe | Phe | 3-Th |
| 13 | —OCH$_2$— | | H | OH | Phe | 3-Fu |
| 14 | H | H | H | OH | 6,2-Pye | 3-Th |
| 15 | H | H | H | Et | Phe | 3-Fu |
| 16 | —CH$_2$CH$_2$— | | OMe | OH | Phe | 3-Fu |
| 17 | H | H | H | OH | 6,2-Pye | 3-Fu |
| 18 | H | H | H | OH | 2,4-Pye | 3-Fu |
| 19 | H | H | H | OH | 4,2-Pye | 3-Fu |
| 20 | —CH$_2$O— | | H | OH | 6,2-Pye | 3-Fu |
| 21 | —CH$_2$O— | | H | OH | 2,4-Pye | 3-Fu |
| 22 | —CH$_2$O— | | H | OH | 4,2-Pye | 3-Fu |
| 23 | —CH$_2$O— | | H | OH | 6,2-Pye | 3-Th |

ASSAYS FOR DETERMINING BIOLOGICAL ACTIVITY

Compounds of Formula I can be tested using the following assays to determine their mammalian leukotriene biosynthesis inhibiting activity.

HUMAN 5-LIPOXYGENASE INHIBITOR SCREEN

Objective of the Assay: The objective of the assay is to select agents which specifically inhibit the activity of human 5-lipoxygenase using a 100,000x g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions, and phosphatidylcholine.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1) containing the coding region sequence for human 5-lipoxygenase is prepared as described by Denis et al. (J. Biol. Chem., 226, 5072-79 (1991)). The enzymatic activity is measured, using a spectrophoto-metric assay from the optimal rate of conjugated diene formation ($A_{234}$) using the procedure described by Riendeau et al. (Biochem. Pharmacol., 38, 2323-2321, 1989) with minor modifications. The incubation mixture contains 50 mM sodium phosphate pH 7.4, 0.2 mM ATP, 0.2 mM CaCl$_2$, 20 $\mu$M arachidonic acid (5 $\mu$L from a 100-fold concentrated solution in ethanol), 12 $\mu$g/mL phosphatidylcholine, an aliquot of the 100,000×g fraction (2-10 $\mu$L) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length, and 4 mm internal width) and the absorbance changes are recorded with a Hewlett-Packard diode array spectrophotometer (HP 8452A) connected to the ChemStation using UV/VIS Kinetics Software (Hewlett-Packard). Enzymatic activity is calculated from the optimal rate of the reaction by a linear fit of the variation of $A_{234}$ during the first twenty seconds using the least square method for the equation $A_{234} = V_o t + A_o$ where $V_o$ is the rate, t is the time and $A_0$ is the absorbance at zero time. The results are expressed as percentages of inhibition of the reaction rate relative to controls (typically between 0.15–0.21 AU/min) containing the DMSO vehicle.

RAT PERITONEAL POLYMORPHONUCLEAR (PMN) LEUKOCYTE ASSAY

Rats under ether anesthesia are injected (i.p.) with 8 mL of a suspension of sodium caseinate (6 g in ca. 50 mL water). After 15–24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350×g, 5min.), resuspended in buffer with vigorous shaking, filtered through lens paper, recentrifuged and finally suspended in buffer at a concentration of 10 cells/mL. A 500 $\mu$L aliquot of PMN suspension and test compound are pre-incubated for 2 minutes at 37°, followed by the addition of 10 $\mu$M calcium ionohphore A-23187. The suspension is stirred for an additional 4 minutes then bioassayed for $LTB_4$ content by adding an aliquot to a second 500 $\mu$L portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

HUMAN POLYMORPHONUCLEAR (PMN) LEUKOCYTE $LTB_4$ ASSAY

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum, A., Scand J. Clin. Lab. Invest., 21 (Supp 97), 77 (1968). Contaminating erythrocytes are removed by lysis following exposure to ammonium chloride (0.16M) in Tris buffer (pH 7.65), and the PMNs resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4. Viability is assessed by Trypan blue exclusion.

B. Generation and Radioimmunoassay of $LTB_4$. PMNs (0.5 mL; $2.5 \times 10^5$ cells) are placed in plastic tubes and incubated (37° C., 2 min) with test compounds at the desired concentration or vehicle (DMSO, final concentration 0.2%) as control. The synthesis of $LTB_4$ is initiated by the addition of calcium ionophore A23187 (final concentration 10 $\mu$M) or vehicle in control samples and allowed to proceed for 5 minutes at 37° C. The reactions are then terminated by the addition of cold methanol (0.25 mL) and samples of the entire PMN reaction mixture are removed for radioimmunoassay of $LTB_4$.

Samples (50 $\mu$L) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-$LTB_4$ (10 nCi in 100 $\mu$L RIA buffer) and $LTB_4$-antiserum (100 $\mu$L of a 1:3000 dilution in RIA buffer) are added and the tubes vortexed. Reactants were allowed to equilibrate by incubation overnight at 4° C. To separate antibody-bound from free $LTB_4$, aliquots (50 $\mu$L) of activated charcoal (3% activated charcoal in RIA buffer containing 0.25% Dextran T-70) are added, the tubes vortexed, and allowed to stand at room temperature for 10 minutes prior to centrifugation (1500×g; 10 min; 4° C.). The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al., Prestaglandins Leukotrienes and Medicine, 13, 21 (1984). The amount of $LTB_4$ produced in test and control samples is calculated. Inhibitory dose-response curves are constructed using a four-parameter algorithm and from these the $IC_{50}$ values are determined.

ASTHMATIC RAT ASSAY

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 L/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

PULMONARY MECHANICS IN TRAINED CONSCIOUS SQUIRREL MONKEYS

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65 HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of Ascaris antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of Ascaris antigen response by the test compound. For statistical analysis, paired t-test is used. (See: McFarlane, C. S. et al., Prostaglandins, 28:173–182, 1984, and McFarlane, C. S. et al., Agents Actions 22:63–68, 1987.)

PREVENTION OF INDUCED BRONCHOCONSTRICTION IN ALLERGIC SHEEP

A. Rationale

Certain allergic sheep with known sensitivity to a specific antigen (Ascarissuum) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance and specific lung resistance.

B. Methods

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of Ascaris suum extract (Greer Diagnostics, Lenois, N.C.) and b) they have previously responded to inhalation challenge with Ascaris suum with both an acute bronchoconstriction and a late bronchial obstruction (Abraham, W. M. et al., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop ®, Puritan Bennett), which produces an aerosol with a mass median aerodynamic diameter of 6.2 $\mu M$ (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challenge. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis: A Kruskal-Wallis one way ANOVA test is used to compare the acute immediate responses to antigen and the peak late response in the controls and the drug treated animals.

PREPARATION OF BENZYL HALIDES

Halide 1

3-[4-(4-Methoxy)tetrahydropyranyl]benzyl bromide

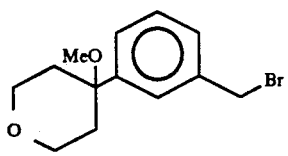

Step 1: 3-[4-(4-Hydroxy)tetrahydropyranyl]toluene

To a solution of 3-bromotoluene (24.3 ml; Aldrich) in THF (250 mL) stirred at −78° C. was added a solution of n-BuLi in hexane (1.75M; 114 mL). After 45 min., the resulting white suspension was treated with a solution of tetrahydropyran-4-one (18.5 mL; Aldrich) in THF (125 mL). After 45 min. at −78° C., the mixture was stirred for 1.5 hr. at room temperature (r.t.). Saturated aqueous $NH_4Cl$ was then added and the organic phase separated. The aqueous phase was extracted with EtOAc. The combined organic phases were washed with brine, dried ($MgSO_4$) and evaporated. Flash chromatography of the residue (silica gel; hexane/EtOAc (1:1)) followed by crystallization in hexane/EtOAc afforded the title compound as a white solid.

Step 2: 3-[4-(4-Methoxy)tetrahydropyranyl]toluene

To a 0° C. solution of the alcohol from Step 1 (38 g) in DMF (300 mL) were added NaH (60% in mineral oil; 16 g) and methyl iodide (31 mL). The mixture was stirred under nitrogen at room temperature for 15 hr. before $H_2O$ (1 L) was added. The aqueous phase was extracted with EtOAc and the combined organic phases were washed with brine, dried ($MgSO_4$) and evaporated. Flash chromatography of the residue (silica gel; hexane/EtOAc, 4:1) yielded the title ether as a colorless liquid.

Step 3: 3-[4-(4-Methoxy)tetrahydropyranyl]benzyl bromide

A mixture of the toluene (16 g) from Step 2, N-bromosuccinimide (14.6 g) and azoisobutyronitrile (AIBN) (127 mg) in $CCl_4$ (250 mL) was refluxed for 1.5 hr. Filtration and evaporation of the filtrate gave the desired benzyl bromide.

Halide 2

3-[4-(4-Hydroxy)tetrahydropyranyl]benzyl bromide

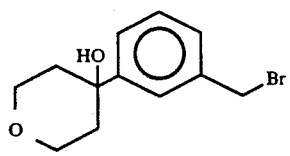

Following the procedure described for Halide 1, Step 3, but substituting 3-[4-(4-hydroxy)tetrahydropyranyl]toluene (from Halide 1, Step 1) for 3-[4-(4-methoxy)tetrahydropyranyl]toluene, the title product was obtained as a yellow solid.

Halide 3

3-[3-(3α-Hydroxy-8-oxabicyclo[3.2.1]oct-6-enyl)]benzyl chloride

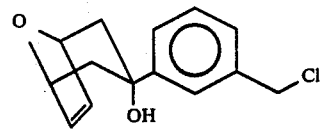

Step 1: 3-Bromo-O-tetrahydropyranylbenzyl alcohol

To a solution of 3-bromobenzyl alcohol (11.5 g; Aldrich) dissolved in $CH_2Cl_2$ (100 mL) at 0° C. and p-toluenesulfonic acid monohydrate (116 mg) was added 6.2 mL of DHP. The resulting solution was stirred at room temperature for 3 hr. then was quenched with $NH_4OAc$. The aqueous phase was extracted with $CH_2Cl_2$. The combined organic phases were washed with brine, dried ($MgSO_4$) and evaporated. Flash chromatography of the residue (silica gel: hexane/EtOAc, 9:1) afforded the title compound as an oil.

Step 2: 3-[3-(3α-Hydroxy-8-oxabicyclo[3.2.1]oct-6-enyl)-O-tetrahydropyranyl]benzyl alcohol Following the procedure described in Halide 1, Step 1, but substituting 3-bromo-O-tetrahydropyranylbenzyl alcohol from Step 1 for 3-bromotoluene, and substituting 8-oxabicyclo[3.2.1]oct-6-en-3-one (J. Amer. Chem. Soc., 100, 1765 (1978)) for tetrahydropyran-4-one, the title compound was obtained.

Step 3: 3-[3-(3α-Hydroxy-8-oxabicyclo[3.2.1]oct-6-enyl)]benzyl alcohol

A solution of the THP derivative (600 mg) from Step 2, in 8 mL of EtOH and pyridinium p-toluenesulfonate (18 mg) was heated at 55° C. for 3 hours. Evaporation of the solvent followed by a flash column (hexane/EtOAc, 1:1) gave the title compound.

Step 4: 3-[3-(3α-Hydroxy-8-oxabicyclo[3.2.1]oct-6-enyl)]benzyl chloride

To a solution of the alcohol (300 mg, 1.3 mmol) obtained from Step 3, in $CH_2Cl_2$ (5 mL) and $CCl_4$ (144 μL) was added $Ph_3P$ (407 mg). The reaction was heated overnight at 70° C. The reaction was diluted with 10% EtOAc in hexane and flash chromatographed directly to give the title compound.

Halide 4

3-[3-(3α-Hydroxy-8-oxabicyclo[3.2.1]octanyl)]benzyl bromide

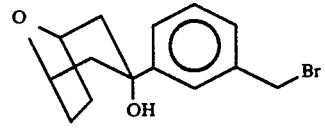

Step 1: 3-[3-(3α-Hydroxy-8-oxabicyclo[3.2.1]oct-6-enyl)toluene

Following the procedure described in Halide 1, Step 1, but substituting 8-oxabicyclo[3.2.1]oct-6-en-3-one (J.A.C.S., 100, 1765 (1978)) for tetrahydropyran-4-one, the title compound was obtained.

Step 2: 3-[3-(3α-Hydroxy-8-oxabicyclo[3.2.1]octanyl)toluene

A mixture of the bicyclic alkene (1.50 g) from Step 1 and 10% Pd/C (0.5 g) in EtOAc (150 mL) and MeOH (15 mL) was stirred under hydrogen at r.t. for 18 hr. The reaction mixture was then filtered over celite and evaporation of the filtrate afforded a yellow waxy solid. Trituration in ether followed by filtration and evaporation of the filtrate then gave a white solid. Purification by flash chromatography (silica gel; hexane/EtOAc, 3:1) yielded the title toluene.

Step 3: 3-[3-(3α-Hydroxy-8-oxabicyclo[3.2.1]octanyl)benzyl bromide

A mixture of the toluene (0.39 g) from Step 2, NBS (0.33 g) and benzoyl peroxide (10 mg) in $CCl_4$ (10 mL) was refluxed and irradiated with visible light for 1.5 h. Filtration and evaporation of the filtrate gave the title benzyl bromide.

Halide 5

3-[4-(4-Methyl)tetrahydropyranyl]benzyl bromide

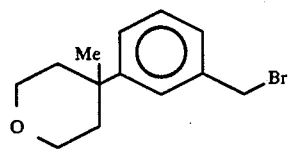

Step 1: 3-[4-(4-Chloro)tetrahydropyranyl]toluene

A solution of 3-[4-(4-hydroxy)tetrahydropyranyl]toluene (Halide 1, Step 1) 0.57 g in $CHCl_3$ (10 mL) was added to a slurry of $P_2Cl_5$ (1.92 g) and $K_2CO_3$ (0.41 g) in $CHCl_3$ (10 mL) stirred at 0° C. for 35 min. The reaction mixture was filtered and evaporation of the filtrate afforded the title compound as a yellow semi-solid.

Step 2: 3-[4-(4-Methyl)tetrahydropyranyl]toluene

To a 0° C. solution of the chloride (452 mg, Step 1) in $CH_2Cl_2$ (7 mL) was added a solution of trimethylaluminum in hexane (2.0M; 2.2 mL; Aldrich). The mixture was stirred at r.t. for 19 hr. before saturated $NaHCO_3$ was added. The aqueous phase was extracted twice with $CH_2Cl_2$ and the combined organic phases were dried ($MgSO_4$) and evaporated. Flash chromatography of the residue (silica gel; hexane/EtOAc, 9:1) yielded the title compound as a colorless liquid.

Step 3: 3-[4-(4-Methyl)tetrahydropyranyl]benzyl bromide

Following the procedure described in Halide 1, Step 3, but substituting the toluene from Step 2 for 3-[4-(4-methoxy)tetrahydropyranyl)toluene, the title product was obtained as an oil.

Halide 6

3-[4-(4-Ethyl)tetrahydropyranyl]benzyl bromide

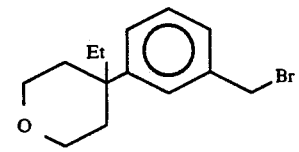

Following the procedure described in Halide 5, Steps 2-3, but substituting triethylaluminum for trimethylaluminum, the title benzyl bromide was obtained as an oil.

Halide 7

3-[3-(3α-Hydroxy-2-methoxy-8-oxabicyclo-[3.2.1]octanyl)]benzyl chloride

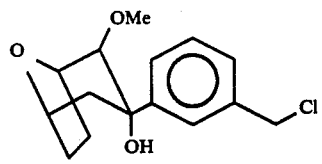

Step 1: 3-[3-(3α-Hydroxy-2-methoxy-8-oxabicyclo[3.2.1]octan-6-enyl)-O-tetrahydropyranyl]-benzyl alcohol Following the procedure described in Halide 1, Step 1, but substituting 3-bromo-O-tetrahydropyranyl benzyl alcohol (from Halide 3, Step 1) for 3-bromotoluene, and substituting 2-methoxy-8-oxabicyclo[3.2.1]oct-6-en-3-one (Tet. Lett., 1990, 31, 4109) for tetrahydropyran-4-one, the title compound was obtained.

Step 2: 3-[3-(3α-Hydroxy-2-methoxy-8-oxabicyclo[3.2.1]octanyl)-O-tetrahydropyranyl]benzyl alcohol Following the procedure described in Halide 4, Step 2, but substituting the bicyclic alkene derivative from Step 1 for 3-[3-(3α-hydroxy-8-oxabicyclo[3.2.1]oct-6-enyl)-O-tetrahydropyranyl]benzyl alcohol, the title compound was obtained.

Step 3: 3-[3-(3α-Hydroxy-2-methoxy-8-oxabicyclo[3.2.1]octanyl)]benzyl chloride

Following the procedure described in Halide 3, Steps 3-4, but substituting the THP derivative from Step 2 for 3-[3-(3α-hydroxy-8-oxabicyclo[3.2.1]octanyl)-O-tetrahydropyranyl]benzyl alcohol, the title compound was obtained.

PREPARATION OF ALCOHOLS

Alcohol 1

5-[4-(4-Hydroxy)tetrahydropyranyl]pyridin-3-ylmethanol

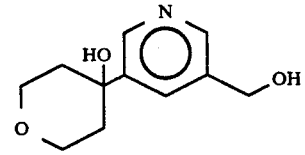

Step 1: 5-Bromo-O-tert-butyldiphenylsilylpyridin-3-ylmethanol

To a solution of 5-bromopyridin-3-ylmethanol (Chem. Pharm. Bull. 1990, 38, 2446) (29 g, 154 mmoL) and tert-butylchlorodiphenylsilane (47.5 g, 173 mmoL) in $CH_2Cl_2$ (500 mL) at r.t., there was added imidazole (15.8 g, 232 mmoL). The mixture was stirred for 1 hr. and filtered. The filtrate was evaporated and the residue chromatographed on silica gel eluting with a 1:7 mixture of EtOAc and hexane, to afford the product as a colorless oil.

Step 2: 5-[4-(4-Hydroxy)tetrahydropyranyl]-O-tertbutyldiphenylsilylpyridin-3-ylmethanol To a solution of the silylether from Step 1 (50 g, 117 mmoL) in THF (500 mL), cooled to −70° C., there was slowly added n-BuLi 1.12M in hexanes (115 mL, 129 mmoL) affording a dark brown solution. To this, there was added a solution of tetrahydro-4H-pyran-4-one (14.1 g, 141 mmoL) in THF (925 mL). The resulting mixture was stirred for 1 hr. at −70° C., then quenched slowly with saturated aqueous NH₄Cl (50 mL) and allowed to warm up to r.t. After diluting with EtOAc (500 mL) the mixture was washed (4×) with brine, dried over Na₂SO₄ and evaporated. Chromatography on silica gel, eluting with EtOAc, afforded the product as an oil which solidified.

Step 3: 5-[4-(4-Hydroxy)tetrahydropyranyl]pyridin-3-ylmethanol

To a solution of the silylether from Step 2 (20.35 g, 45.5 mmoL) in THF (350 mL), there was added Bu₄NF 1M in THF (52 mL) and the mixture was stirred at r.t. for 1 hr. The solvent was evaporated and the residue chromatographed as a short column of silica gel, eluting with a 1:4 mixture of EtOH and EtOAc to afford the title product which was obtained, after trituration with Et₂O and filtration, as a light yellow solid; m.p. 145°–147° C.

Alcohol 2

6-[4-(4-Hydroxy)tetrahydropyranyl]-pyridin-2-ylmethanol

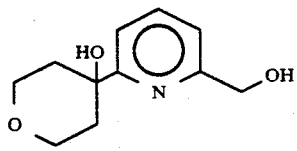

Step 1: 2-Bromo-6-[4-(4-hydroxy)tetrahydropyranyl]-pyridine

A solution of 2,6-dibromopyridine (15 g) in Et₂O (375 mL) was cooled to −78° C. To the resulting suspension was slowly added n-BuLi 2M in hexanes (47.5 mL, 0.9 eq.) and the resulting mixture was stirred for a further 15 min. at −78° C. There was slowly added a solution of tetrahydro-4H-pyran-4-one (11.6 g) in Et₂O (25 mL). The resulting white suspension was stirred at −78° C. for an additional 15 min. There was added saturated aqueous NH₄Cl (100 mL) and the mixture was allowed to warm up to r.t. After dilution with EtOAc, the organic phase was washed (4×) with brine, dried and evaporated. The residue was triturated with Et₂O and filtered to afford the title product as a white solid; m.p. 131°–133° C.

Step 2: 6-[4-(4-Hydroxy)tetrahydropyranyl]pyridin-2-ylmethanol

To a solution of the bromo derivative from Step 1 (7.7 g) in THF (50 mL) and Et₂O (150 mL), cooled to 0° C., there was slowly added n-BuLi 2M in hexanes (30 mL) affording a red-brown suspension. An inlet tube above the surface of the mixture was connected to a flask in which paraformaldehyde (25 g) was gently heated at 175° C. to generate formaldehyde. When all the paraformaldehyde had been decomposed, to the reaction mixture was added saturated aqueous NH₄Cl (100 mL) and EtOAc (500 mL). The organic phase was washed (4×) with brine, dried and evaporated to a residue which was chromatographed on silica gel, eluting with EtOAc to afford the title product as a thick yellow oil.

Alcohol 3

(1S, 5R) 3-[3-(3α-Hydroxy-6,8-dioxabicyclo[3.2.1]octanyl)]benzyl alcohol

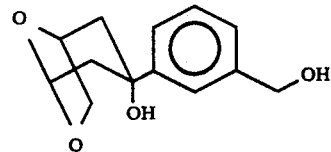

Step 1: 3-Bromo-O-tert-butyldiphenylsilylbenzyl alcohol

To a solution of 3-bromobenzyl alcohol (25 g, 134 mmoL) in anhydrous DMF (300 mL) was added triethylamine (17.6 g, 174 mmoL) followed by t-butyldiphenylsilyl chloride (40.4 g, 147 mmoL). The mixture was stirred for 24 hr., poured into a saturated aqueous NH₄Cl solution (1 L), and extracted with Et₂O. The combined organic layers were washed with brine, dried over MgSO₄ and evaporated. Flash chromatography on silica gel (2.5% EtOAc in hexane) afforded the title compound as a colorless oil.

Step 2: 2,4-Di-O-p-toluenesulfonyl-1,6-anhydro-β-D-glucose

To a solution of 1,6-anhydro-β-D-glucose (50 g, 308 mmoL) in dry pyridine (100 mL) at 0° C. was added dropwise to a solution of p-toluenesulfonyl chloride (123 g, 647 mmoL) dissolved in CHCl₃ (350 mL) and pyridine (200 mL). The reaction mixture was stirred at r.t. for at least 2 days. Water was added and the reaction mixture was stirred for ~1 hr, then the organic layer was decanted and the aqueous phase was re-extracted with CHCl₃. The combined organic layers were washed with H₂SO₄ (10%) until the pH remained acidic, then finally washed with a saturated NH₄OAc solution. The resulting organic layer was dried over MgSO₄ and the solvent evaporated. The syrup obtained was flash chromatographed on silica gel eluting with hexane:EtOAc (1:1) to give the title compound as an oil.

Step 3: (1S,3S,5R) 6,8-Dioxabicyclo[3.2.1]octan-3-ol

The ditosylate derivative from Step 1 (107 g 0.228 mmoL) was dissolved in THF (1.6 L) at −40° C. and Super-Hydride in THF (800 mL, 1M, 0.8 mmoL) was slowly added. The resulting reaction mixture was stirred at r.t. overnight. The reaction was cannulated into cold H₂O (226 mL) using external cooling, then NaOH 3N (640 mL, 1.92 mmol) and H₂O₂ (30%) (490 mL, 4.3 mmol) were successively added. The reaction was stirred at r.t. for 1 hr. Then the supernatant (THF layer) was separated from the aqueous layer and concentrated. The resulting residue was combined with the aqueous layer and extracted with CH₂Cl₂ using a continuous extractor. The organic layer was dried (MgSO₄) and evaporated to dryness. The oily residue was dissolved in hot Et₂O, filtered and evaporated to dryness affording the title compound contaminated with the 2-octanol isomer. The crude product was used as such for the next step.

Step 4: (1S,5R) 6,8-Dioxabicyclo[3.2.1]octan-3-one

The crude alcohol from Step 2 (16.6 g, 89 mmoL) in CH₂Cl₂ (200 mL) was added slowly to a suspension of PCC (38.4 g, 178 mmoL) and celite (22 g) in CH₂Cl₂ (400 mL) and stirred for 1 hr. The reaction mixture was diluted with Et₂O (600 mL) and filtered over celite. The filtrate was evaporated and the residue distilled with a Kügelrohr apparatus (100/C, 1.8 mm/Hg) affording the title product as an oil.

Step 5: (1S,5R) 3-[3α-Hydroxy-6,8-dioxabicyclo[3,2,1]octanyl]benzyl alcohol

Following the procedure described in Halide 1, Step 1, but substituting 3-bromo-O-tert-butyldiphenylsilylbenzyl alcohol (from Step 1) for 3-bromotoluene, and (1S,5R) 6,8-dioxabicyclo[3.2.1.]octan-3-one (from Step 4) for tetrahydropyran-4-one, the tert-butyldiphenylsilylether derivative of the title compound was obtained. The crude product was treated with 1 equivalent of Bu₄NF in dry THF at r.t. for 1.5 hr. After evaporation of the solvent, the crude product was flash chromatographed on silica gel (hexane:EtOAc, 4:1) to afford the pure title product as a colorless oil.

Alcohol 4

(1R,5S) 3-[3-(3α-Hydroxy-6,8-dioxabicyclo[3.2.1]octanyl)]benzyl alcohol

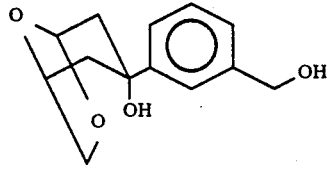

Step 1: (R)3-tert-Butyldimethylsilyloxy-1,2-epoxypropane

To a 0° C. mixture of tert-butyldimethylsilyl chloride (12.2 g) and imidazole (11.5 g) in CH₂Cl₂ (100 mL) was slowly added (S)-Glycidol (5.0 g; Aldrich). After 2.5 hr. at 0° C., the reaction mixture was treated with saturated aqueous NH₄Cl and the organic phase was separated. The aqueous phase was extracted with CH₂Cl₂ (100 mL) and the combined organic phases were washed with H₂O and brine and then dried (MgSO₄) and evaporated. Flash chromatography of the residue (silica gel; hexane/EtOAc, 9:1) afforded the title epoxide as a colorless liquid.

Step 2: (2R) 6,6-Dimethoxy-4-(1,3-propanediyldithio)3-tert-butyldimethylsilyloxyhexan-1-ol To a solution of 2-(2,2-dimethoxyethyl)1,3-dithiane (10.4 g; Liebigs Ann. Chem. 1989, 1045) in THF (50 mL) stirred at −30° C. was added a solution of n-BuLi in hexane (1.3M; 38.5 mL; Aldrich). After 1 hr., the resulting purple solution was treated with a solution of the epoxide (9.4 g) from Step 1 THF (10 mL). After 3 hr at −30° C., the reaction mixture was quenched with saturated aqueous NH₄Cl. Water was then added and the aqueous phase was extracted with Et₂O (2×). The combined organic phases were washed with H₂O and brine, dried (MgSO₄) and evaporated. Flash chromatography of the residue (silica gel; hexane/EtOAc, 4:1) afforded the title alcohol as a yellow liquid.

Step 3: (2R) 6,6-Dimethoxy-4-(1,3-propanediyldithio)hexan-1,2-diol

To a solution of the silyl ether from Step 2 (9.94 g) in THF (50 mL) was added a solution of Bu₄NF in THF (1.0M; 26.5 mL; Aldrich). After 90 min. at r.t., the volatiles were evaporated. Flash chromatography of the residue (silica gel; hexane/EtOAc, 1:3) afforded the title diol as an amber oil.

Step 4: (2R) 6-Hydroxy-2-hydroxymethyl-3-(1,3-propanediyldithio)tetrahydropyran

A solution of the diol from Step 3 (3.11 g) in THF (40 mL) and aqueous HCl (5% v/v; 25 mL) was stirred at 60° C. for 18 hr. Water was then added and the aqueous phase was extracted with EtOAc (3×). The combined organic phases were washed with brine, dried (Na₂SO₄) and evaporated to afford the crude title compound as an amber gum.

Step 5: (2R) 6-Hydroxy-3-(1,3-propanediyldithio)-p-toluenesulfonylmethyl tetrahydropyrane p-Toluenesulfonyl chloride (1.98 g; Aldrich) was added to a 0° C. solution of the alcohol from Step 4 (2.05 g) in pyridine (10 mL). The mixture was stirred at r.t. for 90 min. before MeOH (1 mL) and CHCl₃ (50 mL) were added. The organic phase was washed with H₂O (2×), dried (MgSO₄) and evaporated. Flash chromatography of the residue (silica gel; hexane/EtOAc, 3:2) yielded the title tosylate as an amber semi-solid.

Step 6: (1R,5S) 3-(1,3-Propanediyldithio)-6,8-dioxabicyclo[3.2.1]octane 1,8-Diazabicyclo[5.4.0]undec-7-ene (1.5 mL; Aldrich) was added to a solution of the tosylate from Step 5 (1.95 g) in CH₂Cl₂ (30 mL). The mixture was stirred at r.t. for 16 hr. before the volatiles were evaporated. Flash chromatography of the residue (silica gel; hexane/EtOAc, 3:1) gave the title compound as a white solid.

Step 7: (1R,5S) 6,8-Dioxabicyclo[3.2.1]octan-6-one

To a vigorously stirred mixture of the dithioketal from Step 6 (0.76 g) and CaCo₃ (0.42 g) in THF (12 mL) and H₂O (2.3 mL) was added in 10 min. a solution of Mercury (II) perchlorate trihydrate (1.73 g; Aldrich) in H₂O (1 mL). The mixture was stirred for 40 min. at r.t. before another portion of mercury salt solution (0.56 g in 0.2 mL of H₂O) was slowly added. After 15 min., Et₂O (50 mL) was added and the reaction mixture was filtered. The organic filtrate was dried (MgSO₄) and evaporated to afford the title ketone as an amber liquid.

Step 8: (1R,5S) 3-[3-(3α-Hydroxy-6,8-dioxabicyclo[3.2.1]octanyl)]benzyl alcohol

Following the procedure described in Alcohol 3, Step 5, but substituting 3-bromo-O-tert-butyldiphenylsilyl benzyl alcohol (from Alcohol 3, Step 1) for 3-bromotoluene and (1R,5S) 6,8-dioxabicyclo[3.2.1]octane-3-one (from Step 7) for tetrahydropyran-4-one, the tert butyldiphenylsilylether derivative of the title compound was obtained. The crude product was treated with 1 equivalent of Bu₄NF in dry THF at r.t. for 1.5 hr. After evaporation of the solvent, the crude product was flash chromatographed on silica gel (hexane:EtOAc, 4:1) to afford the pure title product as a colorless oil.

PREPARATION OF LACTONES

Lactone 1

3-Hydroxymethyl-4-(3-furyl)-7-hydroxy-2-naphthoic acid, lactone form

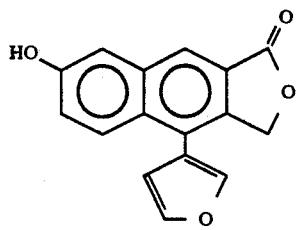

Step 1: 3-Furaldehyde phenyl dithioacetal

To a solution of 3-furaldehyde (28.8 g) and thiophenol (69.2 g) in isopropyl acetate (300 mL), cooled in an ice-water bath, there was slowly added $BF_3.Et_2O$ (42.6 g). The resulting mixture was stirred in the cold for an additional hour. There was slowly added 10% aqueous $K_2CO_3$ (200 mL) and the phases were separated. The aqueous phase was extracted with EtOAc and the combined organic layers were washed with 10% aq. $K_2CO_3$, then with $H_2O$ (3×), dried and evaporated to an oil, which was used as such.

Step 2: 3-[3-Furyl-bis(phenylthio)methyl]2-(3-benzyloxy-α-hydroxybenzyl)butyrolactone To a solution of the dithioacetal from Step 1 (60.0 g) in THF (500 mL), at −70° C. there was slowly added 2.1M n-BuLi in hexanes (100 mL). The resulting dark solution was stirred for a further 20 min. at −70° C., then there was added dropwise 2-(5H)furanone (Omega Inc., 20.16 g), and 30 min. later, a solution of 3-benzyloxybenzaldehyde (Aldrich, 43.5 g) in THF (175 mL). The mixture was stirred a further hour at −70° C., then there was slowly added glacial HOAc (27 g). The mixture was allowed to warm up to r.t., diluted with $Et_2O$ (500 mL), washed with brine (4×), dried and evaporated. The residue was used as such in the next step.

Step 3: 3-Hydroxymethyl-4-(3-furyl)-7-hydroxy-2-naphthoic acid, lactone form

The crude product from Step 2 was dissolved in thioanisole (125 mL), there was added TFA (200 mL) and the mixture was stirred at r.t. for 18 hr. After cooling, the TFA was evaporated, the residue was diluted with $Et_2O$ (400 mL) and after 20 min., the insoluble solid was filtered to afford the desired title compound.

Lactone 2

3-Hydroxymethyl-4-(3-pyridyl)-7-hydroxy-2-naphthoic acid, lactone form

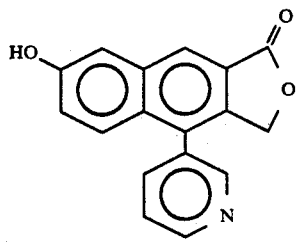

Following the procedure described in Lactone 1, Steps 1–3, but substituting 3-pyridinecarboxaldehyde for 3-furaldehyde, and adding methanesulfonic acid to the trifluoroacetic acid in Step 3, the title compound was obtained.

Lactone 3

3-Hydroxymethyl-4-(2-furyl)-7-hydroxy-2-naphthoic acid lactone form

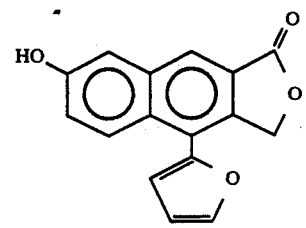

Following the procedure described in Lactone 1, Steps 1–3, but substituting 2-furaldehyde for 3-furaldehyde, the title compound was obtained.

Lactone 4

3-Hydroxymethyl-4-(3-thienyl)-7-hydroxy-2-naphthoic acid, lactone form

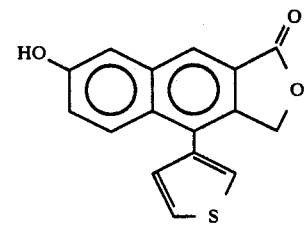

Following the procedure described in Lactone 1, Steps 1–3, but substituting 3-thiophenecarboxaldehyde for 2-furaldehyde, the title compound was obtained.

The invention is further defined by reference to the following examples, which are intended to be illustrative and not limiting. All temperatures are in degrees Celsius.

EXAMPLE 1

3-Hydroxymethyl-4-(3-furyl)-7-[3-[4-(4-hydroxy)tetrahydropyranyl]benzyloxy]-2-naphthoic acid, sodium salt Step 1: 3-Hydroxymethyl-4-(3-furyl)-7-[3-[4-(4-hydroxytetrahydropyranyl]benzyloxy]-2-naphthoic acid, lactone form A mixture of 3-[4-(4-hydroxy)tetrahydropyranyl]benzyl bromide (Halide 2) (355 mg), 3-hydroxymethyl-4-(3-furyl)-7-hydroxy-2-naphthoic acid, lactone form (Lactone 1) (333 mg), and $Cs_2CO_3$ (426 mg) in DMF (10 mL) was stirred at r.t. overnight. To the reaction mixture was added $H_2O$ (2 mL) followed by EtOAc (100 mL) and the organic layer separated. The aqueous layer was extracted with EtOAc and the combined organic layers were washed with $H_2O$, brine, dried over $MgSO_4$ and evaporated. The residue was flash chromatographed on silica gel eluting with hexane:EtOAc:$CH_2Cl_2$ (1:1:1) to afford the title compound as a white solid; m.p. 181°–183° C.

Step 2: 3-Hydroxymethyl-4-(3-furyl)-7-[3-[4-(4-hydroxy)tetrahydropyranyl]benzyloxy]-2-naphthoic acid, sodium salt To a suspension of the lactone from Step 1 (500 mg) in EtOH (10 mL) was added 1N NaOH (1.1 mL, 1 eq.) and refluxed for 18 hr. The resulting solution was evaporated to dryness to afford the title salt as a foam.

$^1$NMR (300 MHz, acetone-$d_6$) δ3.7 (m, 2H), 3.85 (m, 2H), 4.5 (s, 2H), 4.85 (s, 2H), 6.4 (s, 1H), 7.0 (m, 1H), 7.15 (m, 2H), 7.25 (m, 1H), 7.5 (m, 4H), 8.35 (s, 1H).

EXAMPLE 2

3-Hydroxymethyl-4-(3-furyl)-7-[3-[4-(4-methoxy)tetrahydropyranyl]benzyloxy]-2-naphthoic acid, sodium salt Step 1: 3-Hydroxymethyl-4-(3-furyl)-7-[3-[4-(4-methoxy)tetrahydropyranyl]benzyloxy]-2-naphthoic acid, lactone form Following the procedure described in Example 1, but substituting 3-[4-(4-methoxy)tetrahydropyranyl]benzyl bromide (Halide 1) for 3-[4-(4-hydroxy)tetrahydropyranyl]benzyl bromide (Halide 2), the title compound was obtained as a solid; m.p. 179°–181° C.

Step 2: 3-Hydroxymethyl-4-(3-furyl)-7-[3-[4-(4-methoxytetrahydropyranyl]benzyloxy]-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 3

3-Hydroxymethyl-4-(3-pyridyl)-7-[3-[4-(4-hydroxy)tetrahydropyranyl]benzyloxy]-2-naphthoic acid, sodium salt Step 1: 3-Hydroxymethyl-4-(3-pyridyl)-7-[3-[4-(4-hydroxy)tetrahydropyranyl]benzyloxy]-2-naphthoic acid, lactone form Following the procedure described in Example 1, but substituting 3-hydroxymethyl-4-(3-pyridyl)-7-hydroxy-2-naphthoic acid, lactone form (Lactone 2) for 3-hydroxy-methyl-4-(3-furyl)-7-hydroxy-2-naphthoic acid (Lactone 1), lactone form, the title compound was obtained as a yellow solid; m.p. 219°–222° C.

Step 2: 3-Hydroxymethyl-4-(3-pyridyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 4

3-Hydroxymethyl-4-(2-furyl)-7-[3-[4-(4-hydroxy)tetrahydropyranyl]benzyloxy]-2-napthoic acid, sodium salt Step 1: 3-Hydroxymethyl-4-(2-furyl)-7-[3-[4-(4-hydroxy)tetrahydropyranyl]benzyloxy]-2-naphthoic acid, lactone form Following the procedure described in Example 1, but substituting 3-hydroxymethyl-4-(2-furyl)-7-hydroxy-2-naphthoic acid, lactone form (Lactone 3) for 3-hydroxymethyl-4-(3-furyl)-7-hydroxy-2-naphthoic acid, lactone form (Lactone 1), the title compound was obtained as a solid; m.p. 164°–166° C.

Step 2: 3-Hydroxymethyl-4-(2-furyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 5

3-Hydroxymethyl-4-(3-furyl)-7-[3-[3-(3α-hydroxy-8-oxabicyclo[3.2.1]oct-6-enyl)]benzyloxy]-2-naphthoic acid, sodium salt Step 1: 3-Hydroxymethyl-4-(3-furyl)-7-[3-[3-(3α-hydroxy-8-oxabicyclo[3.2.1]oct-6-enyl)]benzyloxy]-2-naphthoic acid, lactone form Following the procedure described in Example 1, but substituting 3-[3-(3α-hydroxy-8-oxabicyclo[3.2.1]oct-6-enyl]benzyl chloride (Halide 3) for 3-[4-(4-methoxy)tetrahydropyranyl]benzyl bromide (Halide 1), the title compound was obtained as a solid; m.p. 222°–223° C.

Step 2: 3-Hydroxymethyl-4-(3-furyl)-7-[3-[3-(3α-hydroxy-8-oxabicyclo[3.2.1]oct-6-enyl)]benzyloxy]-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product was obtained as a foam.

$^1$H NMR (300 MHz, DMSO-$d_6$) δ1.6 (d, 2H); 2.1 (dd, 2H); 4.3 (s, 2H); 4.5 (s, 1H); 4.7 (d, 2H); 5.2 (s, 2H); 6.3 (s, 2H); 6.6 (s, 1H); 7.1 (dd, 1H); 7.3–7.4 (m, 3H); 7.4 (d, 1H); 7.5 (d, 1H); 7.6 (s, 1H); 7.7 (s, 1H); 7.9 (t, 1H); 8.0 (s, 1H).

EXAMPLE 6

3-Hydroxymethyl-4-(3-furyl)-7-[3-[3-(3α-hydroxy-8-oxabicyclo[3.2.1]octanyl)]benzyloxy]-2-naphthoic acid, sodium salt Step 1: 3-Hydroxymethyl-4-(3-furyl)-7-[3-[3-(3α-hydroxy-8-oxabicyclo[3.2.1]octanyl)]benzyloxy]-2-naphthoic acid, lactone form Following the procedure described in Example 1, but substituting 3-[3-(3α-hydroxy-8-oxabicyclo[3.2.1]octanyl)]benzyl chloride (Halide 4) for 3-[4-(4-methoxy)-tetrahydropyranyl]benzyl bromide (Halide 1), the title compound was obtained as a solid; m.p. 195°–200° C.

Step 2: 3-Hydroxymethyl-4-(3-furyl)-7-[3-[3-(3α-hydroxy-8-oxabicyclo[3.2.1]octanyl)]benzyloxy]-2-naphthoic acid, sodium salt Following the procedure described in Example 1, Step 2, but substituting the lactone from Step 1 for 3-hydroxymethyl-4-(3-furyl)-7-[3-[4-(4-hydroxy)tetrahydropyranyl]benzyloxy]-2-naphthoic acid, lactone form, the title product was obtained as a foam.

$^1$H NMR (300 MHz, DMSO-$d_6$) δ1.6–1.8 (m, 4H); 2.0 (dd, 2H); 2.3 (d, 2H); 4.2–4.5 (m, 4H); 5.0 (s, 1H); 5.2 (s, 2H); 6.6 (s, 1H); 7.1 (dd, 1H); 7.3–7.4 (m, 3H); 7.9 (d, 1H); 7.5 (d, 1H); 7.6 (s, 1H); 7.7 (s, 1H); 7.9 (s, 1H); 8.0 (s, 1H).

EXAMPLE 7

3-Hydroxymethyl-4-(3-furyl)-7-{5-[4-(4-hydroxy)tetrahydropyranyl]pyridin-3-ylmethoxy}-2-naphthoic acid, sodium salt Step 1: 3-Hydroxymethyl-4-(3-furyl)-7-{5-[4-(4-hydroxy)tetrahydropyranyl]pyridin-3-ylmethoxy}-2-naphthoic acid, lactone form To a mixture of 3-hydroxymethyl-4-(3-furyl)-7-hydroxy-2-naphthoic acid, lactone form (Lactone 1) (293 mg), 5-[4-(4-hydroxy)tetrahydropyranyl]pyridin-3-ylmethanol (Alcohol 1) (209 mg), and triphenylphosphine (315 mg) in THF (10 mL), there was added di-tert-butyl azodicarboxylate (276 mg) and the mixture was stirred at r.t. for 2 hr. After evaporation of the THF, the residue was flash chromatographed on silica gel, eluting with EtOAc. The product obtained was triturated with ether affording on filtration the title compound as a beige solid; m.p. 122° C. (dec).

Step 2: 3-Hydroxymethyl-4-(3-furyl)-7-{5-[4-(4-hydroxy)tetrahydropyranyl]pyridin-3-ylmethoxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 8

(1S, 5R)
3-Hydroxymethyl-4-(3-furyl)-7-{3-[3-(3α-hydroxy-6,8-dioxabicyclo[3.2.1]octanyl)]benzyloxy}-2-naphthoic acid, sodium salt Step 1: (1S, 5R) 3-Hydroxymethyl-4-(3-furyl)-7-{3-[3-(3α-hydroxy-6,8-dioxabicyclo[3.2.1]-octanyl)]benzyloxy}-2-naphthoic acid, lactone form Following the procedure described in Example 7, but substituting (1S, 5R) 3-[3-(3α-hydroxy-6,8-dioxabicyclo[3.2.1]octanyl)]benzyl alcohol (Alcohol 3) for 5-[4-(4-hydroxy)tetrahydropyranyl]pyridin-3-ylmethanol (Alcohol 1), the title compound was obtained as a solid; m.p. 223° C.

Step 2: (1S, 5R) 3-Hydroxymethyl-4-(3-furyl)-7-{3-[3-(3α-hydroxy-6,8-dioxabicyclo[3.2.1]-octanyl)]benzyloxy}-2-naphthoic acid, sodium salt Following the procedure described in Example 1, Step 2, but substituting the lactone from Step 1 for 3-hydroxymethyl-4-(3-furyl)-7-[3-[4-(4-hydroxy)tetrahydropyranyl]benzyloxy]-2-naphthoic acid, lactone form, the title product was obtained as a foam.

$^1$H NMR (300 MHz, DMSO-d$_6$) δ1.8 (d, 1H); 2.0 (dq, 2H); 2.2 (dd, 1H); 3.6 (t, 1H), 4.3 (br-s, 2H); 4.4 (d, 1H); 4.6 (t, 1H); 5.1 (s, 1H); 5.2 (s, 2H); 5.6 (s, 1H); 6.6 (s, 1H); 7.1 (dd, 1H); 7.3–7.4 (m, 3H); 7.4 (d, 1H); 7.5 (d, 1H); 7.6 (s, 1H); 7.7 (s, 1H); 7.9 (t, 1H); 8.0 (s, 1H).

EXAMPLE 9

3-Hydroxymethyl-4-(3-thienyl)-7-{3-[4-(4-hydroxy)tetrahydropyranyl]benzyloxy}-2-naphthoic acid, sodium salt Step 1: 3-Hydroxymethyl-4-(3-thienyl)-7-{3-[4-(4-hydroxy)tetrahydropyranyl]benzyloxy}-2-naphthoic acid, lactone form Following the procedure described in Example 1, but substituting 3-hydroxymethyl-4-(3-thienyl)-7-hydroxy-2-naphthoic acid, lactone form (Lactone 4) for 3-hydroxymethyl-4-(3-furyl)-7-hydroxy-2-naphthoic acid, lactone form (Lactone 1), the title compound was obtained as a solid; m.p. 172°–175° C.

Step 2: 3-Hydroxymethyl-4-(3-thienyl)-7-[3-[4-(4-hydroxy)tetrahydropyranyl]benzyloxy]-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product was obtained as a foam.

$^1$H NMR (300 MHz, acetone-d$_6$) δ3.7 (m, 2H), 3.85 (m, 2H), 4.4 (m, 2H), 4.8 (s, 2H), 6.95 (m, 2H), 7.15 (m, 3H), 7.25 (m, 2H), 7.45 (m, 2H); 7.55 (s, 1H), 8.4 (s, 1H).

EXAMPLE 10

3-Hydroxymethyl-4-(3-thienyl)-7-{5-[4-(4-hydroxy)tetrahydropyranyl]pyridin-3-ylmethoxy}-2-naphthoic acid, sodium salt Step 1: 3-Hydroxymethyl-4-(3-thienyl)-7-{5-[4-(4-hydroxy)tetrahydropyranyl]pyridin-3-ylmethoxy}-2-naphthoic acid, lactone form Following the procedure described in Example 7, but substituting 3-hydroxymethyl-4-(3-thienyl)-7-hydroxy-2-naphthoic acid, lactone form (Lactone 4) for 3-hydroxymethyl-4-(3-furyl)-7-hydroxy-2-naphthoic acid, lactone form (Lactone 1), the title compound was obtained as a white solid.

$^1$H NMR (250 MHz, CDCl$_3$) δ1.74 (m, 2H), 1.84 (s, 1H, OH), 2.23 (m, 2H), 3.95 (m, 4H), 5.26 (s, 2H), 5.32 (s, 2H), 7.20–7.60 (m, 5H), 7.90 (d, 1H), 8.00 (s, 1H), 8.37 (s, 1H), 8.68 (s, 1H), 8.78 (s, 1H).

Step 2: 3-Hydroxymethyl-4-(3-thienyl)-7-{5-[4-(4-hydroxy)tetrahydropyranyl}pyridin-3-ylmethoxy]-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 11

(1S, 5R)
3-Hydroxymethyl-4-(3-thienyl)-7-{3-(3α-hydroxy-6,8-dioxabicyclo[3.2.1]octanyl)]benzyloxy}-2-naphthoic acid, sodium salt Step 1: (1S, 5R)
3-Hydroxymethyl-4-(3-thienyl)-7-{3-(3α-hydroxy-6,8-dioxabicyclo[3.2.1]-octanyl)]benzyloxy}-2-naphthoic acid, lactone form Following the procedure described in Example 7, but substituting (1S, 5R) 3-[3-(3α-hydroxy-6,8-dioxabicyclo[3.2.1]octanyl)]benzyl alcohol (Alcohol 3) for 5-[4-(4-hydroxy)tetrahydropyranyl]pyridin-3-ylmethanol (Alcohol 1), and substituting 3-hydroxymethyl-4-(3-thienyl)-7-hydroxy-2-naphthoic acid, lactone form (Lactone 4) for 3-hydroxymethyl-4-(3-furyl)-7-hydroxy-2-naphthoic acid, lactone form (Lactone 1), the title compound was obtained as a solid; m.p. 221°–222° C.

Step 2: (1S, 5R) 3-Hydroxymethyl-4-(3-thienyl)-7-{3-(3α-hydroxy-6,8-dioxabicyclo[3.2.1]octanyl)]benzyloxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product was obtained as a foam.

$^1$H NMR (300 MHz, DMSO-d$_6$) δ1.8 (d, 1H); 2.0 (dq, 2H); 2.2 (dd, 1H); 3.6 (t, 1H); 4.2 (s, 2H); 4.4 (d, 1H); 4.6 (t, 1H); 5.1 (s, 1H); 5.2 (s, 2H); 5.6 (s, 1H); 7.1 (m, 2H); 7.2–7.5 (m, 6H); 7.6 (s, 1H); 7.7 (m, 1H); 8.1 (s, 1H).

EXAMPLE 12

(1S, 5R)
3-Hydroxymethyl-4-(3-thienyl)-7-{3-[3-(3α-methoxy-6,8-dioxabicylo[3.2.1]octanyl)]benzyloxy}-2-naphthoic acid, sodium salt Step 1: (1S, 5R) 3-Hydroxymethyl-4-(3-thienyl)-7-{3-[3-(3α-methoxy-6,8-dioxabicylo-[3.2.1]-octanyl)]benzyloxy}-2-naphthoic acid, lactone form To a solution of (1S, 5R) 3-hydroxymethyl-4-(3-thienyl)-7-{3-[3-(3α-hydroxy-6,8-dioxabicyclo[3.2.1]octanyl)]benzyloxy]-2-naphthoic acid, lactone form (Example 11) (200 mg) in dry THF (3 mL) at 0° C. was added KH (35% in mineral oil, 137 mg, 3 eq.) in dry THF (2 mL). After 10 min. methyl iodide (0.1 mL, 4 eq.) was added and the resulting mixture was stirred for 30 min. at 0° C. The reaction mixture was then poured into saturated aqueous NH$_4$Cl and extracted with EtOAc. The organic layer was washed with brine, dried over MgSO$_4$ and evaporated. Flash chromatography on silica gel eluting with EtOAc:hexane (3:7) afforded the title compound as a solid; m.p. 183°–184° C.

Step 2: (1S,5R) 3-Hydroxymethyl-4-(3-thienyl)-7-{3-[3-(3α-methoxy-6,8-dioxabicylo[3.2.1]octanyl)]benzyloxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 13

(1R,5S)
3-Hydroxymethyl-4-(3-furyl)-7-{3-[3-(3α-hydroxy-6,8-dioxabicylo[3.2.1]octanyl)]benzyloxy}-2-naphthoic acid, sodium salt Step 1: (1R,5S) 3-Hydroxymethyl-4-(3-furyl)-7-[3-[3-(3α-hydroxy-6,8-dioxabicylo[3.2.1]octanyl)]benzyloxy]-2-naphthoic acid, lactone form Following the procedure described in Example 7, but substituting (1R,5S) 3-[3-(3α-hydroxy-6,8-dioxabicyclo[3.2.1]octanyl)]benzyl alcohol (Alcohol 4) for 5-[4-(4-hydroxy)tetrahydropyranol]pyridin-3-ylmethanol (Alcohol 1), the title compound was obtained as a foam.

$^1$H NMR (300 MHz, CDCl$_3$): δ2.00–2.12 (m, 2H), 2.30 (d, 1H), 2.48 (dd, 1H), 3.80 (m, 1H), 3.91 (s, 1H), 4.50 (d, 1H), 4.71 (m, 1H), 5.22 (s, 2H), 5.33 (s, 2H), 5.78 (s, 1H), 6.60 (dd, 1H), 7.19 (m, 1H), 7.37–7.40 (m, 4H), 7.65 (m, 3H), 8.01 (d, 1H), 8.33 (s, 1H).

Step 2: (1R,5S) 3-Hydroxymethyl-4-(3-furyl)-7-{3-[3-(3α-hydroxy-6,8-dioxabicylo[3.2.1]octanyl)]benzyloxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 14

3-Hydroxymethyl-4-(3-thienyl)-7-{6-[4-(4-hydroxy)tetrahydropyranyl]pyridin-2-ylmethoxy}-2-naphthoic acid, sodium salt Step 1: 3-Hydroxymethyl-4-(3-thienyl)-7-{6-[4-(4-hydroxy)tetrahydropyranyl]pyridin-2-ylmethoxy}-2-naphthoic acid, lactone form Following the procedure described in Example 7, but substituting 6-[4-(4-hydroxy)tetrahydropyranyl]pyridin-2-yl-methanol (Alcohol 2) for 5-[4-(4-hydroxy)tetrahydropyranyl]-pyridin-3-ylmethanol (Alcohol 1), and substituting 3-hydroxymethyl-4-(3-thienyl)-7-hydroxy-2-naphthoic acid, lactone form (Lactone 4) for 3-hydroxymethyl-4-(3-furyl)-7-hydroxy-2-naphthoic acid, lactone form (Lactone 1), the title compound was obtained as a solid. $^1$H NMR (250 MHz, CDCl$_3$): δ1.6 (m, 2H), 2.15 (m, 2H), 4.0 (m, 4H), 5.15 (s, 1H), 5.3 (s, 2H), 5.35 (s, 2H), 7.2 (dd, 1H), 7.35 (m, 4H), 7.5 (d, 1H), 7.55 (m, 1H), 7.8 (dd, 1H), 7.9 (d, 1H), 8.35 (s, 1H).

Step 2: 3-Hydroxymethyl-4-(3-thienyl)-7-{6-[4-(4-hydroxy)tetrahydropyranyl]pyridin-2-ylmethoxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 15

3-Hydroxymethyl-4-(3-furyl)-7-{3-[4-(4-ethyl)tetrahydropyranyl]benzyloxy}-2-naphthoic acid, sodium salt Step 1: 3-Hydroxymethyl-4-(3-furyl)-7-{3-[4-(4-ethyl)tetrahydropyranyl]benzyloxy}-2-naphthoic acid, lactone form Following the procedure described in Example 1, but substituting 3-[4-(4-ethyl)tetrahydropyranyl]benzyl bromide (Halide 6) for 3-[4-(4-hydroxy)tetrahydropyranyl]benzyl bromide (Halide 2), the title compound was obtained as a pale yellow solid.

$^1$H NMR (250 MHz, CDCl$_3$): δ0.55 (t, 3H), 1.65 (q, 2H), 1.85 (m, 2H), 2.15 (m, 2H), 3.55 (m, 2H), 3.80 (m, 2H), 5.23 (s, 2H), 5.37 (s, 2H), 6.60 (dd, 1H), 7.30–7.45 (m, 6H), 7.65 (m, 2H), 8.02 (d, 1H), 8.33 (s, 1H).

Step 2: 3-Hydroxymethyl-4-(3-furyl)-7-{3-[4-(4-ethyl)tetrahydropyranyl]benzyloxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

EXAMPLE 16

3-Hydroxymethyl-4-(3-furyl)-7-{3-[3-(3α-hydroxy-2-methoxy-8-oxabicyclo[3.2.1]octanyl)]benzyloxy}-2naphthoic acid, sodium salt Step 1: 3-Hydroxymethyl-4-(3-furyl)-7-{3-[3-(3α-hydroxy-2-methoxy-8-oxabicyclo[3.2.1]octanyl)]benzyloxy}-2-naphthoic acid, lactone form Following the procedure described in Example 1, but substituting 3-[3-(3α-hydroxy-2-methoxy-8-oxabicyclo[3.2.1]octanyl)]benzyl chloride (Halide 7) for 3-[4-(4-hydroxy)tetrahydropyranyl]benzyl bromide (Halide 2), the title compound was obtained as a solid; m.p. 185° C.

Step 2: 3-Hydroxymethyl-4-(3-furyl)-7-{3-[3-(3α-hydroxy-2-methoxy-8-oxabicyclo[3.2.1]octanyl)]benzyloxy}-2-naphthoic acid, sodium salt Following the procedure described in Example 1, Step 2, but substituting the lactone from Step 1 for 3-hydroxymethyl-4-(3-furyl)-7-{3-[4-(4-hydroxy)tetrahydropyranyl]benzyloxy}-2-naphthoic acid, lactone form, the title product is obtained.

What is claimed is:

1. A compound of the formula:

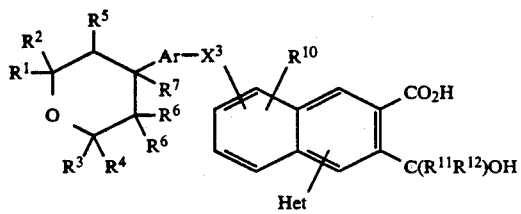

wherein:
- $R^1$, $R^5$, and $R^{11}$ is each independently H, OH, lower alkyl, or lower alkoxy;
- $R^2$ is H, lower alkyl or together with $R^1$ forms a double bonded oxygen (=O);
- $R^3$ is H, lower alkyl, hydroxy lower alkyl, lower alkoxy lower alkyl, or is joined to $R^1$ to form a carbon bridge of 2 or 3 carbon atoms or a mono-oxa carbon bridge of 1 or 2 carbon atoms, said bridge optionally containing a double bond;
- $R^4$, $R^{12}$, and $R^{14}$ is each independently H or lower alkyl;
- $R^6$ is H or lower alkyl, or two $R^6$ groups on the same carbon can form a saturated ring of 3 to 8 members;
- $R^7$ is H, OH, lower alkyl, lower alkoxy, lower alkylthio, or lower alkylcarbonyloxy;
- $R^8$ is H, halogen, lower alkyl, lower alkoxy, $CF_3$, CN, or $COR^{14}$;
- $R^9$ and $R^{10}$ is each independently H, lower alkyl, lower alkoxy, hydroxy lower alkyl, lower alkoxy lower alkyl, lower alkylthio lower alkyl, lower alkylthio lower alkylcarbonyl, $(R^8)_2$-phenylthio lower alkyl, halogen, CN, $NO_2$, $CF_3$, $N_3$, $N(R^{13})_2$, $NR^{13}COR^{14}$, $NR^{13}CON(R^{13})_2$, $SR^{15}$, $S(O)R^{15}$, $S(O)_2R^{15}$, $S(O)_2N(R^{13})_2$, $COR^{14}$, $CON(R^{13})_2$, $CO_2R^{14}$, $C(R^{14})_2OC(R^{14})_2$—$CO_2R^{14}$, or $C(R^{14})_2CN$;
- $R^{10}$ is attached to either ring of the naphthalene ring system;
- $R^{13}$ is H or lower alkyl, or two $R^{13}$ groups attached to the same nitrogen may form a saturated ring of 5 or 6 members, optionally containing a second heteroatom chosen from O, S, or $NR^4$;
- $R^{15}$ is lower alkyl, phenyl-$(R^8)_2$, or $CF_3$;
- $X^3$ is $C(R^6)_2O$ or $OC(R^6)_2$;
- Ar is arylene$(R^8)_2$ wherein arylene is a 5-membered aromatic ring containing one O; a 6-membered aromatic ring; or 2- or 4-pyranone;
- Het is heteroaryl$(R^9)_2$ wherein heteroaryl is a 5-membered aromatic ring containing one O; 2- or 4-pyranone; or a bicyclic 8- or 9-membered aromatic ring containing 1-2 O;
- Het is attached to either ring of the naphthalene ring system; or a pharmaceutically acceptable salt thereof.

2. A compound of claim 1 of the formula:

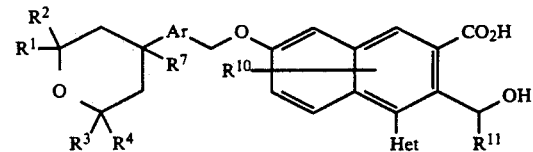

or a pharmaceutically acceptable salt thereof.

3. A compound of claim 1 of the formula:

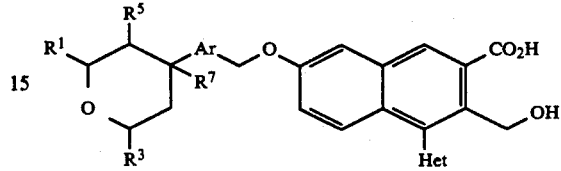

wherein:
- $R^1$ is H, Me, or OMe;
- $R^3$ is H or Me;
- $R^1$ and $R^3$ together are —CH=CH—, —$CH_2CH_2$—, —$OCH_2$—, or —$CH_2O$—;
- $R^5$ is H or $OCH_3$;
- $R^7$ is OH, $OCH_3$, or $CH_2CH_3$;
- Ar is Phe; and
- Het is 3-Fu;

or a pharmaceutically acceptable salt thereof.

4. A compound of claim 3 wherein the substituents are as follows:

| EX | $R^1$ | $R^3$ | $R^5$ | $R^7$ | Ar | Het |
|---|---|---|---|---|---|---|
| 1 | H | H | H | OH | Phe | 3-Fu |
| 2 | H | H | H | OMe | Phe | 3-Fu |
| 4 | H | H | H | OH | Phe | 2-Fu |
| 5 | —CH=CH— | | H | OH | Phe | 3-Fu |
| 6 | —$CH_2CH_2$— | | H | OH | Phe | 3-Fu |
| 8 | —$CH_2O$— | | H | OH | Phe | 3-Fu |
| 13 | —$OCH_2$— | | H | OH | Phe | 3-Fu |
| 15 | H | H | H | Et | Phe | 3-Fu |
| 16 | —$CH_2CH_2$— | | OMe | OH | Phe | 3-Fu |

5. A pharmaceutical composition comprising a therapeutically effective amount of a compound of claim 1 and a pharmaceutically acceptable carrier.

6. A pharmaceutical composition of claim 5 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; $H_1$- or $H_2$-receptor antagonists; antihistaminic agents; prostaglandin antagonists; thromboxane antagonists; thromboxane synthetase inhibitors; and ACE antagonists.

7. A pharmaceutical composition of claim 6, wherein the second active ingredient is a non-steroidal anti-inflammatory drug.

8. A pharmaceutical composition comprising a therapeutically effective amount of a compound of claim 1, an effective amount of a second active ingredient which is a non-steroidal anti-inflammatory drug, and a pharmaceutically acceptable carrier, wherein the weight ratio of said compound of claim 1 to said second active ingredient ranges from about 1000:1 to 1:1000.

9. A method of preventing the synthesis of leukotrienes in a mammal which comprises administering to said mammal an effective amount of a compound of claim 1.

10. A method of claim 9 wherein the mammal is man.

* * * * *